(12) United States Patent
Van Agthoven et al.

(10) Patent No.: US 7,541,190 B2
(45) Date of Patent: Jun. 2, 2009

(54) METHOD OF MEASUREMENT OF CELLULAR HEMOGLOBIN

(75) Inventors: Andreas Van Agthoven, Marseille (FR); Fabrice Malergue, Marseille (FR)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 11/501,395

(22) Filed: Aug. 9, 2006

(65) Prior Publication Data

US 2007/0020612 A1　Jan. 25, 2007

Related U.S. Application Data

(63) Continuation-in-part of application No. 11/052,269, filed on Feb. 7, 2005.

(51) Int. Cl.
　　*G01N 33/72*　　(2006.01)
(52) U.S. Cl. ...................................................... 436/66
(58) Field of Classification Search ....................... None
See application file for complete search history.

(56) References Cited

U.S. PATENT DOCUMENTS

| | | | | |
|---|---|---|---|---|
| 3,552,925 | A * | 1/1971 | Fetter et al. | 436/169 |
| 5,516,695 | A * | 5/1996 | Kim et al. | 436/17 |
| 5,768,303 | A | 6/1998 | Motoda et al. | |
| 5,798,827 | A | 8/1998 | Frank et al. | |
| 6,271,035 | B1 | 8/2001 | Deka et al. | |
| 6,534,279 | B1 * | 3/2003 | Agthoven et al. | 435/7.21 |
| 2003/0025896 | A1 * | 2/2003 | Oever et al. | 356/39 |
| 2004/0214243 | A1 | 10/2004 | Burshteyn et al. | |
| 2006/0178294 | A1 | 8/2006 | Van Agthoven et al. | |

OTHER PUBLICATIONS

Invitrogen web site entry, accessed Jun. 2008, 5 pages.*
Campbell, T.A., et al, "Detection of Hemoglobin Variants in Erythrocytes by Flow Cytometry", Cytometry 35:242-248 (1999).
Goldstein, D.E., et al, "Glycated Hemoglobin: Methodologies and Clinical Applications", Clin Chem 32/10(B), B64-B70 (1986).
Vassar, et al, "Physiocochemical Effects of Aldehydes on the Human Erythrocyte", J Cell Biol, vol. 58, pp. 809-818 (1972).
Berlier, et al, "Quantitative Comparison of Long-wavelength Alexa Fluor Dyes to Cy Dyes: Fluorescence of the Dyes and Their Bioconjugates", Journal of Histochemistry & Cytochemistry, vol. 51(12); 1699-1712, 2003.

* cited by examiner

*Primary Examiner*—Anish Gupta
*Assistant Examiner*—Ronald T Niebauer
(74) *Attorney, Agent, or Firm*—Cuspa Technology Law Associates; Mitchell E. Alter (57) ABSTRACT

A method of measuring cellular hemoglobin of a blood sample includes mixing a blood sample with a permeation reagent, and incubating the sample mixture to permeate cellular membrane of red blood cells and to cause hemoglobin aggregation within the cells; adding a neutralization reagent to inhibit further reactions of the permeation reagent; performing a cell-by-cell measurement of side scatter signals of the red blood cells in the sample mixture on a flow cytometer; and obtaining cellular hemoglobin ($Hgb_{cell}$) of each red blood cell using the obtained side scatter signals. The method further includes measuring cellular hemoglobin of reticulocytes ($Hgb_{retic}$) by differentiating reticulocytes using a simultaneous fluorescence measurement. The method also includes measuring cellular percentage of a hemoglobin variant in mature red blood cells or reticulocytes by adding a fluorescent antibody in the neutralization reagent and detecting fluorescence signals of antibody bound hemoglobin variant.

20 Claims, 5 Drawing Sheets

METHOD OF MEASUREMENT OF CELLULAR HEMOGLOBIN

CROSS REFERENCE TO RELATED APPLICATION

This application is a continuation-in-part of application Ser. No. 11/052,269, filed on Feb. 7, 2005, which is hereby incorporated by reference in its entirety.

FIELD OF THE INVENTION

The present invention relates to a method of measuring cellular hemoglobin and hemoglobin variants of individual mature red blood cells and reticulocytes.

BACKGROUND OF THE INVENTION

The cellular hemoglobin of red blood cells is an important parameter for clinical diagnosis. On hematology analyzers, Mean corpuscular hemoglobin (MCH) of a blood sample is derived from the red blood cell count (RBC) and total hemoglobin (Hgb) of the blood sample. The latter is obtained by a spectrophotometric measurement of hemoglobin concentration of a lysed blood sample. MCH is an average measurement of all red blood cells, it does not represent hemoglobin content of individual red blood cells.

In contrast, the measurement of cellular hemoglobin in a flow cytometer is a cell-by-cell measurement, which provides diagnostic information that is not available through MCH. Campbell et al. *Cytometry* 35, pp 242-248 (1999) have performed flow cytometric analysis of hemoglobin in individual red blood cells using a fluorescent anti-hemoglobin A antibody. Burshteyn et al. (U.S. Patent Application Publication No. 2004/0214243) have performed flow cytometric analysis of hemoglobin using an anti-pan hemoglobin antibody. Since red blood cells have a very high concentration of hemoglobin, in order to measure the total cellular hemoglobin using antibodies, a large amount of fluorescent antibodies are required. Furthermore, there are potential artifacts due to steric hindrance of antibody binding or extinction of fluorescence due to the high density of hemoglobin in the cell. Therefore, it is desirable to have a method that enables the measurement of total cellular hemoglobin without relying on the use of antibodies.

On the other hand, cell-by-cell hemoglobin measurement has been developed in hematology analysis using multi-angle light scatter measurements. To facilitate the light scatter measurement, typically a blood sample is treated with an isotonic, neutral sphering reagent to sphere the red blood cells prior to the measurement. When untreated red blood cells are measured by light scatter measurements, they produce heterogeneous scatter results, because the concave shaped cells can have various different orientations as they pass through the flow cell. Upon mixing with a sphering reagent, the red blood cells are sphered, which can produce homogeneous scatter results. However, the light scatter measurement for determining cellular hemoglobin is complex, typically multiple angles of light scatter signals are utilized. For example, Bayer's hematology analyzers provide a cell-by-cell measurement of red blood cells using a complex light scatter measurement based on Mei theory. Although all commercial available flow cytometers are equipped with forward and side scatter measurement devices, the forward and side scatter signals of sphered red blood cells do not correlate to the cellular hemoglobin, and hence have not been used for quantitative measurement of cellular hemoglobin. Furthermore, the red blood cells treated by sphering reagent are not permeable to large intracellular markers such as antibodies, therefore, not suitable for measurement of hemoglobin variants utilizing antibodies.

Identifying and/or quantifying variants and aberrant forms of hemoglobin are important for clinical diagnosis of various diseases, for example, sickle cell disease, thalassemia and diabetics. The measurement of hemoglobin $A_{1C}$ has been one of most frequently used hemoglobin variant measurement, and is an important clinical measure for diabetic patients.

It is known that about 90% of total hemoglobin is nonglycosylated. The major fraction of nonglycosylated hemoglobin is nonglycosylated $Hb_A$, referred to as $Hb_{A0}$. Glycated hemoglobin refers to a series of minor hemoglobin components that are formed via the attachment of various sugars to the hemoglobin molecule. The human erythrocyte is freely permeable to glucose. Within each erythrocyte, glycated hemoglobin is formed at a rate that is directly proportional to the ambient glucose concentration. The reaction of glucose with hemoglobin is nonenzymatic, irreversible and slow, so that only a fraction of the total hemoglobin is glycated during the life span of an erythrocyte (120 days). As a result, the measurement of glycated hemoglobin provides a weighted "moving" average of blood glucose levels that can be used to monitor long-term blood glucose levels, providing an accurate index of the mean blood glucose concentration over the preceding 2 to 3 months. The most important clinical application of this is in the assessment of glycemic control in a diabetic patient.

Hemoglobin $A_{1C}$ ($Hb_{A1C}$) is one specific type of glycated hemoglobin and is the most important hemoglobin species with respect to diabetes. $Hb_{A1C}$ is approximately 3 to 6% of the total hemoglobin in nondiabetics, and 20% or greater in diabetes that is poorly controlled (Goldstein, et al., *Clin. Chem.* 32: B64-B70, 1986). The determination of the concentration of $Hb_{A1C}$ is useful in diagnosing and monitoring diabetes mellitus.

Based on the above, it is therefore desirable to have a method that enables measurements of total hemoglobin content and specific hemoglobin variant in individual red blood cells at the same time. Moreover, it is further desirable to have a method that enables such a cell-by-cell measurement for different red blood cell subpopulations, such as in both mature red blood cells, and reticulocytes, at the same time.

SUMMARY OF THE INVENTION

In one embodiment, the present invention is directed to a method of measuring cellular hemoglobin of a blood sample. The method comprises mixing a blood sample with a permeation reagent to form a first sample mixture; and incubating the first sample mixture for a first period of time sufficient to permeate cellular membrane of red blood cells and to cause hemoglobin aggregation within the cells; adding a neutralization reagent to the first sample mixture to form a second sample mixture, and incubating the second sample mixture for a second period of time sufficient to inhibit further reactions of the permeation reagent with the red blood cells; performing a cell-by-cell measurement of side scatter signals of the red blood cells in the second sample mixture on a flow cytometer; and obtaining cellular hemoglobin ($Hgb_{cell}$) of the red blood cells of the blood sample using the side scatter signals. The method further comprises adding a fixation reagent into the second sample mixture to fix the red blood cells, prior to measurement on the flow cytometer.

In a further embodiment, the present invention is directed to a method of measurement of cellular hemoglobin of reticulocytes in a blood sample. The method comprises mixing an aliquot of the blood sample with a nucleic acid dye reagent to form a stained sample, and incubating the stained sample for a first period of time sufficient to allow the dye to bind to intracellular RNA; mixing an aliquot of the stained sample with a permeation reagent to form a first sample mixture; and incubating the first sample mixture for a second period of time sufficient to allow the permeation reagent to permeate the cellular membrane of mature red blood cells and reticulocytes and cause hemoglobin aggregation within the cells; adding a neutralization reagent to the first sample mixture to form a second sample mixture; incubating the second sample mixture for a third period of time sufficient to inhibit further reactions of the permeation reagent with the mature red blood cells and the reticulocytes; performing a cell-by-cell measurement of side scatter signals and fluorescence signals at a predetermined wavelength, of the mature red blood cells and the reticulocytes in the second sample mixture on a flow cytometer; differentiating the reticulocytes from the mature red blood cells using the fluorescence signals, or a combination of the fluorescence signals and the side scatter signals; and obtaining cellular hemoglobin ($Hgb_{retic}$) of the reticulocytes using the side scatter measurement.

In another embodiment, the present invention is directed to a method of determining a cellular percentage of a hemoglobin variant of a blood sample. The method comprises mixing an aliquot of the blood sample with a permeation reagent to form a first sample mixture; and incubating the first sample mixture for a first period of time sufficient to allow the permeation reagent to permeate cellular membrane of red blood cells and cause hemoglobin aggregation within the cells; adding a neutralization reagent containing an antibody specific to the hemoglobin variant to the first sample mixture to form a second sample mixture; incubating the second sample mixture for a second period of time sufficient to permit the antibody to bind to the hemoglobin variant within the cells, and inhibiting further reactions of the permeation reagent with the red blood cells; performing a cell-by-cell measurement of side scatter signals and fluorescence signals at a predetermined wavelength, of the red blood cells in the second sample mixture on a flow cytometer; obtaining cellular hemoglobin variant ($Hgb_{variant}$) and cellular hemoglobin ($Hgb_{cell}$) of the red blood cells using the side scatter signals and fluorescence signals obtained; and obtaining cellular percentage of the hemoglobin variant using obtained $Hgb_{variant}$ and $Hgb_{cell}$. The hemoglobin variant comprises glycated hemoglobins, fetal hemoglobin, or aberrant forms of hemoglobin.

In yet a further embodiment, the present invention is directed to a method of measurement of cellular hemoglobin variant of reticulocytes in a blood sample. The method comprises mixing an aliquot of the blood sample with a nucleic acid dye reagent to form a stained sample, and incubating the stained sample for a first period of time sufficient to permit the dye to bind to intracellular RNAs; mixing an aliquot of the stained sample with a permeation reagent to form a first sample mixture; and incubating the first sample mixture for a second period of time sufficient to allow the permeation reagent to permeate cellular membrane of mature red blood cells and reticulocytes and cause hemoglobin aggregation within the cells; adding a neutralization reagent containing an antibody specific to a hemoglobin variant to the first sample mixture to form a second sample mixture; incubating the second sample mixture for a third period of time sufficient to permit binding of the antibody to the hemoglobin variant within the cells, and inhibiting further reactions of the permeation reagent with the mature red blood cells and the reticulocytes; performing a cell-by-cell measurement of fluorescence signals at two predetermined wavelengths of the mature red blood cells and the reticulocytes in the second sample mixture on a flow cytometer; and differentiating the reticulocytes from the mature red blood cells, and obtaining the cellular hemoglobin variant of the reticulocytes using the fluorescence signals.

The cell-by-cell measurement can further include a measurement of side scatter signals of the mature red blood cells and the reticulocytes in the second sample mixture. The method then can further include obtaining cellular hemoglobin of the reticulocytes ($Hgb_{retic}$) using the side scatter signals; and obtaining cellular percentage of the hemoglobin variant of the reticulocytes using the cellular hemoglobin variant and the $Hgb_{retic}$.

In another aspect, the present invention is directed to a flow cytometry reagent system, which comprises an aqueous permeation reagent for permeating cellular membrane of a blood cell and causing aggregation of hemoglobin within the blood cells; and a neutralization reagent comprising a buffer and an osmolality adjusting agent for inhibiting reaction of the permeation reaction with the blood cell. The reagent system can further comprise a fixation reagent. The permeation reagent comprises an effective amount of N-acyl sarcosine or a salt thereof; the reagent having a pH between 4 and 6 and a low ionic strength defined by a conductivity of less than 9.0 mS/cm.

The advantages of the present invention will become apparent from the following description taken in conjunction with the accompanying drawings.

DETAILED DESCRIPTION OF THE INVENTION

In one aspect, the present invention provides a method of measuring cellular hemoglobin of a blood sample using side scatter measurement. Herein, cellular hemoglobin is the amount of hemoglobin (picogram) in individual red blood cells. Cellular hemoglobin ($Hgb_{cell}$) is also commonly referred to as cell-by-cell hemoglobin, as it is obtained by a cell-by-cell measurement.

In one embodiment, the method includes the following steps:

(a) mixing an aliquot of a blood sample with a permeation reagent to form a first sample mixture; and incubating the first sample mixture for a first period of time sufficient to permeate cellular membrane of red blood cells and to cause hemoglobin aggregation within the cells;

(b) adding a neutralization reagent to the first sample mixture to form a second sample mixture, and incubating the second sample mixture for a second period of time sufficient to inhibit further reactions of the permeation reagent with the red blood cells; and (c) performing a cell-by-cell measurement of side scatter signals of the red blood cells in the second sample mixture on a flow cytometer; and (d) obtaining cellular hemoglobin ($Hgb_{cell}$) of the red blood cells using the side scatter signals obtained from the measurement.

Preferably, the method further includes adding a fixation reagent into the second sample mixture to fix the red blood cells, prior to the cell-by-cell measurement.

The permeation reagent used herein is also referred to as a cell permeabilization and stabilization reagent, and its function in permeating cellular membrane and preserving cellular components for flow cytometric measurements has been described in co-pending patent application Ser. No. 11/052,269, which is herein incorporated by reference in its entirety.

In one embodiment, the permeation reagent is an aqueous solution comprising N-acyl sarcosine or a salt thereof represented by the following molecular structure:

wherein $R_1$ is an alkyl or alkylene group having 8 to 18 carbon atoms, and $X_1$ is H, $Na^+$, or $K^+$, and a pH adjusting agent to adjust pH of the reagent less than 7. The permeation reagent is preferably slightly acidic, with a pH in a range from about 4 to about 6. More preferably, pH of the reagent is from about 4.6 to about 5.6.

Preferably, the pH adjusting agent is a strong base or acid, therefore, a small quantity of the chemical can be used to adjust the pH within the desired range. In one preferred embodiment, N-acyl sarcosine free acid is used, and pyrrolidine, a strong organic base, or NaOH, a strong inorganic base, is used to adjust the pH between 4 and 6. If a N-acyl sarcosine salt is used, then a strong acid, such as HCl, can be used to adjust the pH. Furthermore, an organic buffer can be used to maintain the pH. In one exemplary embodiment, succinic acid is used, which has a $pka_1$ of 4.19 and $pKa_2$ of 5.57.

The permeation reagent has a low ionic strength defined by a conductivity of less than 9.0 mS/cm. However, it is only slightly hypotonic, and has an osmolality from about 240 to about 280 mOsm/kg $H_2O$.

It has been found that upon exposing the cells to the permeation reagent, intracellular protein aggregation is more effective under a low ionic strength. For the purpose of the present invention, the ionic strength of the aqueous reagent composition is defined by conductivity of the reagent. It is believed that intracellular protein aggregation is necessary to conserve cell integrity after permeation. When the ionic strength is too high, for example when the conductivity of the reagent is higher than 9 mS/cm, the reagent can no longer aggregate intracellular proteins, and the cells lose their integrity. Preferably, the permeation reagent has a conductivity of less than 1.2 mS/cm. Since ionic compounds, such as salts, are the major contributors of the ionic strength of the reagent, it is preferred to have low salt concentration in the reagent.

N-acyl sarcosine, in a free acid form, and the salt thereof are commercially available. It is preferred to use the free acid form, which does not introduce metal ions into the reagent. N-acyl sarcosine in a free acid form is not water soluble. It can be pre-dissolved in an ethanol solution, and then added into the aqueous solution. When pH of the reagent is adjusted between 4 and 6 by a pH adjusting agent, N-acyl sarcosine can be dissolved and is present in the form of anion in the solution.

Suitable examples of N-acyl sarcosine include N-oleoyl sarcosine, N-stearoyl sarcosine, N-lauroyl sarcosine, N-myristoyl sarcosine, N-cocoyl sarcosine, and salts thereof. Preferably, the alkyl or alkylene group of $R_1$ has 12 carbon atoms. In one preferred embodiment, N-lauroyl sarcosine is used.

In further embodiment, the permeation reagent can further comprise an anionic surfactant represented by following molecular structure:

wherein $R_2$ is an alkyl or alkylene group having 8 to 18 carbon atoms; and $X_2$ is $Na^+$, $K^+$, $NH_4^+$, or $NH_2C(CH_2OH)_3$ (i.e., tris(hydroxymethyl)-aminomethane). Preferably, the alkyl or alkylene group of $R_2$ of the anionic surfactant has 12 carbon atoms. Suitable examples include sodium, potassium, ammonium and tris(hydroxymethyl)aminomethane lauryl sulfates. In a preferred embodiment, tris(hydroxymethyl)aminomethane lauryl sulfate is used, which is referred to as Tris lauryl sulfate hereinafter.

In the permeation reagent, N-acyl sarcosine or the salt thereof, or in combination with the alkyl or alkylene sulfate surfactant, is in a sufficient amount to enable the reagent permeating the cellular membrane and enabling penetration of intracellular markers, while substantially preserving the cellular membrane and the cellular constituents for specific bindings with their cellular markers for analysis by flow cytometry. It has been found that both surfactant concentrations can be in a range from about 0.01 mM to 100 mM, preferably 0.1 mM to 10 mM, and more preferably 1 mM to 5 mM. In one exemplary embodiment, 2.3 mM of N-lauroyl sarcosine was used. In another example, a mixture of 0.5 mM of Tris lauryl sulphate and 2.2 mM of N-lauroyl sarcosine was used.

The surfactant(s) in the concentration described above have the property of causing aggregation of polypeptides and proteins at a slightly acidic pH, which does not denature the intracellular antigen sites, and does not destroy the cellular membrane.

Preferably, the permeation reagent further comprises bovine serum albumin (BSA). Bovine serum albumin enhances solubility of the surfactant in the aqueous solution, and is beneficial for long term use and storage of the permeation reagent.

Optionally, the permeation reagent can further comprise an organic osmolality adjusting agent. Suitable examples of the osmolality adjusting agent include, but are not limited to, saccharide, ethylene glycol, dimethylsulphoxide, or glycerol. Preferably, saccharide or glycerol is used. The saccharide can be a polysaccharide, such as a disaccharide, or a monosaccharide. In one exemplary embodiment as shown in Composition D of Example 1, sucrose is used.

Furthermore, the permeation reagent can further comprise one or more preservatives. Suitable examples include antimicrobials and antioxidants, for extension of shelf life of the reagent. The preservative can be present in an amount that does not interfere with the function of the reagent. In one embodiment, 5-chloro-2-methyl-4-isothiazolin-3-one and 2-methyl-4-isothiazolin-3-one are used as antimicrobials. Combinations of 5-chloro-2-methyl-4-isothiazolin-3-one and 2-methyl-4-isothiazolin-3-one manufactured by Rohm and Hass, Philadelphia, Pa., are available commercially under the trade name Proclin® 150 and Proclin® 300.

Example 1 shows four exemplary compositions of the permeation reagent of the present invention.

It has been found that when mixed with blood cells, the permeation reagent of the present invention effectively permeates the cellular membrane which enables penetration of intracellular markers into the cell for subsequent cellular analysis; and the permeation reagent also causes intracellular protein aggregation within the cells. At the same time, however, the permeation reagent preserves the cellular constituents, such as intracellular and cell surface antigen sites, DNA and RNA molecules, and cytoskeleton elements, for binding with intracellular markers. Upon permeation, the red blood cells are also sphered, which enables accurate measurement of red blood cells by light scatter measurements, without the effects of cell shape and orientation.

For the purpose of the present invention, the term "cellular constituent" includes cellular components inside the cells, and on the surface of the cellular membrane such as cell surface antigen sites. While the term "intracellular constituent" refers to a cellular component inside the cells, which includes, but is not limited to, intracellular proteins, such as hemoglobin and hemoglobin variants inside the red blood cells, cytoskeleton elements, DNA and RNA. The cytoskeleton elements include, but are not limited to, tubulin and spectrin. The term of "cellular marker" used herein includes, but is not limited to, an antibody specific to an antigen site of an intracellular protein, a cell surface antigen site, or a cytoskeleton element; a nucleic acid dye and a nucleic acid probe specific to a DNA or a RNA molecule, such as an oligonucleotide probe. Preferably, the cellular marker is labeled with a fluorescent dye. Furthermore, the cellular marker specific to an intracellular constituent is also referred to as an intracellular marker.

Figure 1:
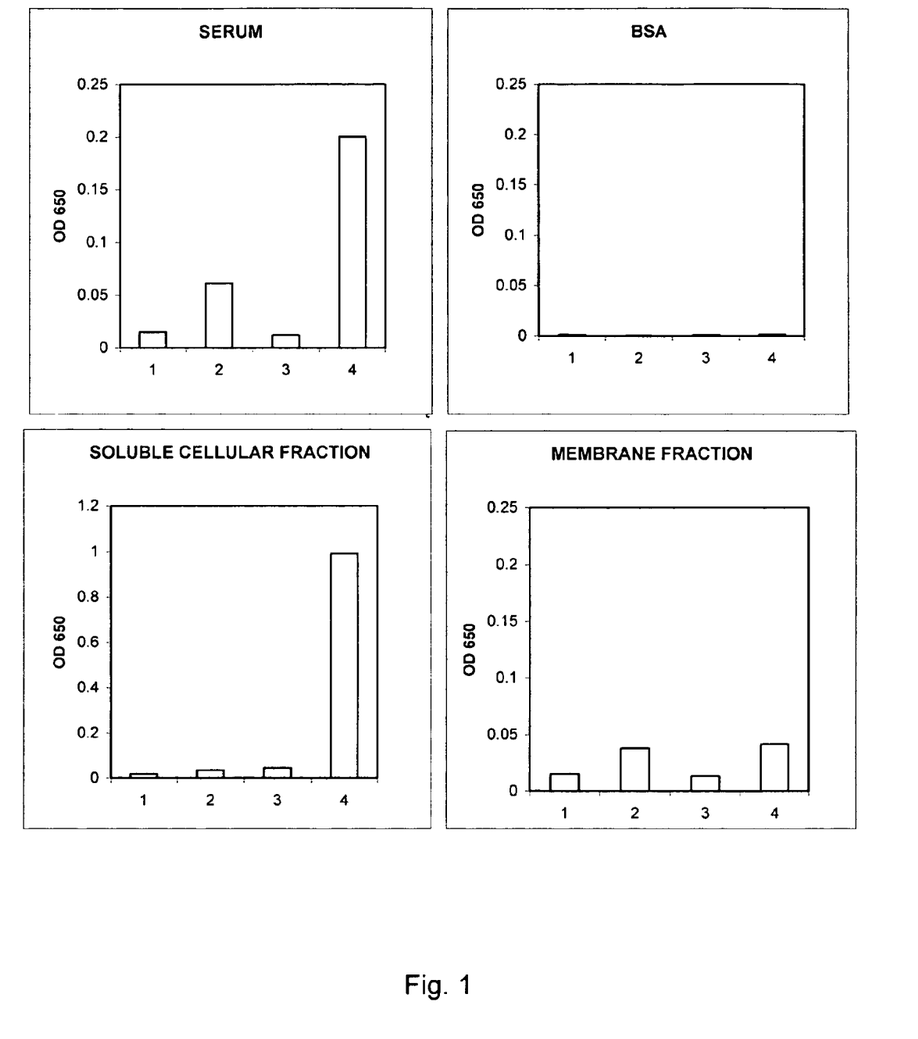
FIG. 1 shows the effect of the permeation reagent on precipitation of proteins in different fractions of the blood: top left, serum; top right, bovine serum albumin; bottom left, soluble cell fraction and bottom right, membrane fraction.

Example 6 illustrates the effect of the permeation reagent on protein aggregation using Composition C of Example 1. FIG. 1 shows the effect of the permeation reagent on the precipitation of the serum components, the soluble cellular fraction (cytosol) and a membrane preparation as described in Example 6. In each preparation, with the exception of the bovine serum albumin, the optical density of the mixture of the cellular fractions and the permeation reagent increased substantially due to protein aggregation. The optical density increased most in the soluble cell fraction, because of the presence of high concentration of hemoglobin in the soluble cell fraction. It is noted that the optical density was measured at 650 nm, at which hemoglobin does not absorb. Therefore, the increase of optical density was caused by the opacity of the mixture. In the membrane fraction, the increase in optical density was less, which can be understood that the result was masked by the dissolution of the lipid parts of the membranes by the surfactant. Furthermore, this example showed that the presence of bovine serum albumin in the permeation reagent, such as in Composition D of Example 1, would not affect the opacity of a sample mixture.

Preferably, a blood sample is mixed with the permeation reagent with a dilution ratio about 200:1 to about 8000:1. The blood sample is incubated with the permeation reagent for a period time to facilitate the reaction of the permeation reagent with the cells. Preferably, the incubation time is from about 30 seconds to about 5 minutes, more preferably, from about 2 minutes to about 3 minutes.

Thereafter, the permeation reaction is stopped by addition of a neutralization reagent. The neutralization reagent is hypertonic and essentially neutral, with a pH slightly above 7.0. When mixed with the first sample mixture, the neutralization reagent brings pH of the sample mixture to neutral, and increases the ionic strength and osmolality of the sample mixture. As such, it effectively inhibits further reaction of the permeation reagent.

The neutralization reagent comprises an osmolality adjusting agent and a buffer. Preferably, osmolality adjusting agent is one or more alkaline metal salt, preferably alkaline metal halides, such as sodium or potassium chloride. The osmolality of the neutralization reagent is preferably from about 800 to about 1,200 mOsm/kg $H_2O$. The buffer can be an organic or inorganic buffer, which provides a neutral pH. The pH of the neutralization reagent is preferably from about 7.1 to about 7.5, more preferably from about 7.2 to about 7.4.

Furthermore, the neutralization reagent can further comprise bovine serum albumin. Bovine serum albumin assists in preserving integrity of the cellular constituents, particularly the intracellular antigen sites, such as the antigen sites of glycated hemoglobin ($Hb_{A1c}$) or fetal hemoglobin ($Hb_F$) for their binding with respective antibodies. Preferably, the concentration of bovine serum albumin is from about 0.4 to about 1.2 mM.

Moreover, the neutralization reagent further comprises an antimicrobial. In one exemplary embodiment, sodium azide is used. Sodium azide is a strong antimicrobial, which is particularly suitable for the neutralization reagent as it has a neutral pH and contains high concentration of bovine serum albumin. Example 2 illustrates an exemplary composition of the neutralization reagent.

Preferably, the neutralization reagent as shown in Example 2 is used with a ration to the permeation reagent of about 1.5 to about 1.8. After the addition of the neutralization reagent, the formed second sample mixture is further incubated for a period time to effectively stop the reaction of the permeation reagent and stabilize the sample mixture. This incubation time is preferably from about 5 minutes to about 30 minutes, and more preferably from about 8 minutes to about 12 minutes. Thereafter, the second sample mixture can be aspirated and measured on a flow cytometric instrument equipped with side scatter detection means for measurement.

When a specific hemoglobin variant is to be measured, for example in the measurement of $Hb_{A1c}$ as described in detail hereinafter, an antibody specific to the hemoglobin variant of interest can be added into the neutralization reagent. As the cell membrane is permeated by the permeation reagent, these large antibody molecules can penetrate through cellular membrane and bind to the antigen sites of the intracellular proteins.

Typically, the sample mixtures are measured on a flow cytometer in a batch by batch manner. The prepared sample mixtures might wait for a substantial period of time before the measurement, for example, a couple of hours. Therefore, in the instant method, a fixation reagent can be further added to the second sample mixture to fix the cells.

The fixation reagent comprises a fixative, an osmolality adjusting agent and a buffer. Preferably, the fixative is an aldehyde, including, but not limited to, formaldehyde, paraformaldehyde, or glutaraldehyde. The osmolality adjusting agent can be one or more alkaline metal salt, preferably alkaline metal halides, such as sodium or potassium chloride. Preferably, the fixation reagent is hypertonic, with an osmolality from about 1,100 to about 1,400 mOsm/kg $H_2O$. The buffer can be an organic or inorganic buffer, which provides a neutral pH. The pH of the fixation reagent is preferably from about 6.9 to about 7.3, which maintains the neutral pH achieved by the neutralization reagent.

Furthermore, preferably the fixation reagent further comprises chelating agents such as dextran sulfate, EGTA, and boric acid. It has been found that the combination of dextran sulfate, EGTA and boric acid in the fixation reagent can effectively prevents cell aggregation in the final sample mixture, in comparison to the commonly used fixing reagent comprising formaldehyde and phosphate buffered saline. Example 3 shows an exemplary composition of the fixation reagent.

As described hereinbefore, the present invention provides a reagent system for preparing blood samples for measurement of hemoglobin and its variants on a flow cytometer. The reagent system comprises the permeation reagent and the neutralization reagent described above, and preferably further comprises the fixation reagent.

Example 7 illustrates the method of the present invention for measuring cellular hemoglobin using side scatter measurement. Herein, the term of side scatter signal, as known in flow cytometry, refers to the light scatter signal at about 90° or at the right angle from the incident light, generated by a particle or a blood cell passing through the aperture of a flow cell. The forward scatter signal refers to the light scatter signal measured less than 10° from the incident light. The term of side scatter measurement refers to the measurement of the side scatter signals by an optical detector. All commercially available flow cytometers are equipped with a detection system which enables measurement of the forward scatter and side scatter signals.

It is noted that in Example 7, a sphering reagent is used to mix with the blood sample prior to the addition of the permeation reagent. As can be appreciated from the further embodiments of the present invention described hereinafter, in the measurement of cellular hemoglobin of the reticulocytes the nucleic acids in the reticulocytes are stained. This is accomplished using a nucleic acid dye reagent which has this sphering reagent as the medium. To provide a common sample preparation process for the measurements of cellular hemoglobin in both mature red blood cells and reticulocytes, the sphering reagent is used prior to the reaction of the blood sample with the permeation reagent. However, it should be understood that mixing with the sphering reagent is not needed for the measurement of cellular hemoglobin of a blood sample when differentiation of reticulocytes is not required, because the permeation reagent of the present invention itself spheres the red blood cells, as described above.

Figure 2A:
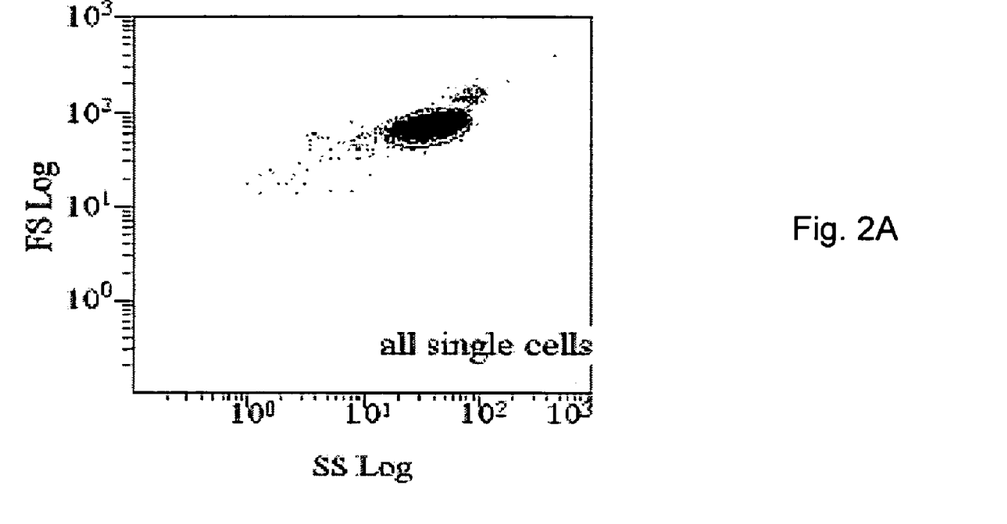
FIGS. 2A and 2B show the scattergrams of forward scatter vs. side scatter (in log scale) of a blood sample obtained using the method of the present invention, and using a sphering reagent treatment, respectively.

As shown, 16 clinical whole blood samples were prepared using the process of the present invention. The prepared sample mixtures were analyzed on a FC500 MPL flow cytometer. The obtained scattergram of forward scatter vs. side scatter of one blood sample is shown in FIG. 2A. In the scattergram, the major population of measured blood cells was the treated red blood cells. The mean side scatter value of each blood sample was obtained in this population.

Figure 2B:
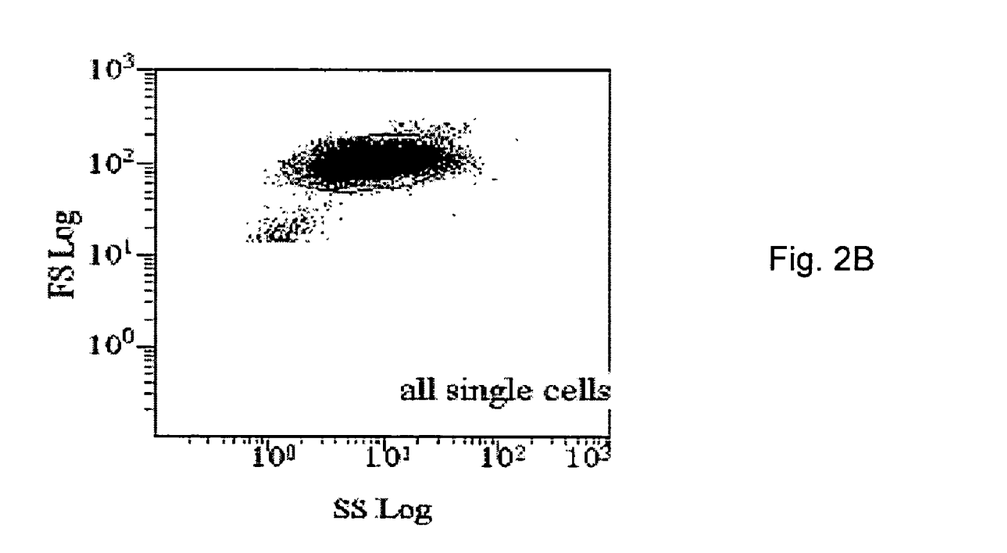

For the purpose of comparison, another aliquot from each of these 16 samples was prepared using the sphering reagent, without the reagent system of the present invention. 4 µl of a blood sample was mixed with 200 µl of the sphering reagent of Example 4. After 1 minute of incubation, 3 µl of the suspension was mixed with 240 µl of phosphate buffered saline (PBS) to form a sphered sample. The sphered sample was analyzed on the same FC500 MPL cytometer. FIG. 2B showed the scattergram of forward scatter vs. side scatter of the same blood sample shown in FIG. 2A.

As shown, the mean side scatter value of the blood sample obtained using the method of the present invention was substantially higher than the mean side scatter value of the blood sample obtained using the treatment of the sphering reagent and PBS. Among these 16 blood samples, the mean side scatter values obtained using the method of the present invention were in average about 4 to 5 times higher.

These 16 whole blood samples were also analyzed on a Sysmex XE 2100 hematological analyzer. The mean corpuscular hemoglobin (MCH) was obtained for each of the blood samples from the red cell index reported by the analyzer. It is noted that on the hematology analyzer, MCH (picogram) was calculated from the total hemoglobin concentration (Hgb, gram/deciliter) of a lysed blood sample and the red blood cell count (RBC, number/liter) of the blood sample.

Figure 3A:
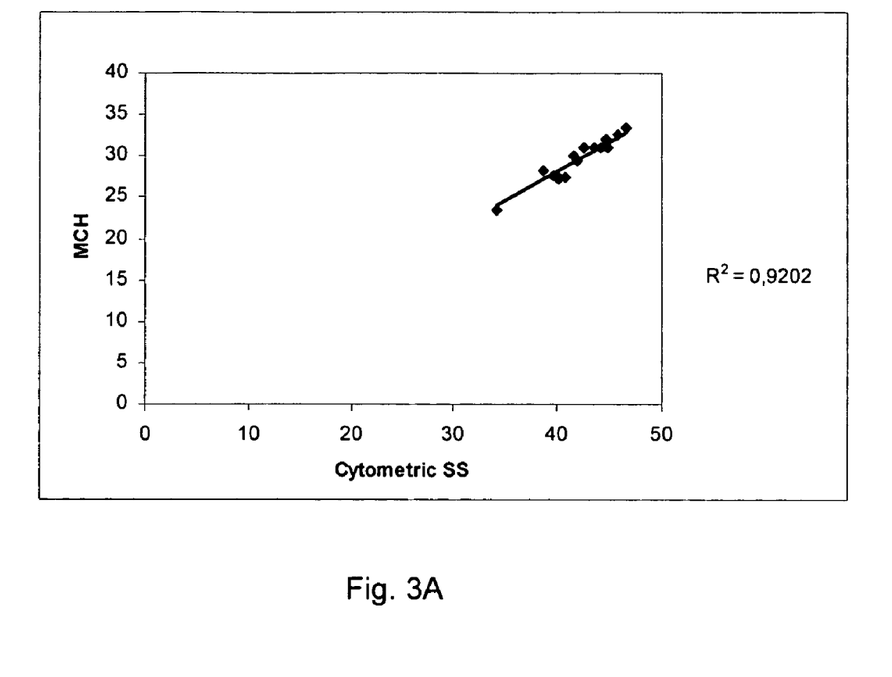
FIG. 3A shows a linear correlation curve of the mean side scatter values (labeled as Cytometric SS) of 16 blood samples obtained using the instant method and the MCH values of the same blood samples reported on a hematological analyzer.
Figure 3B:
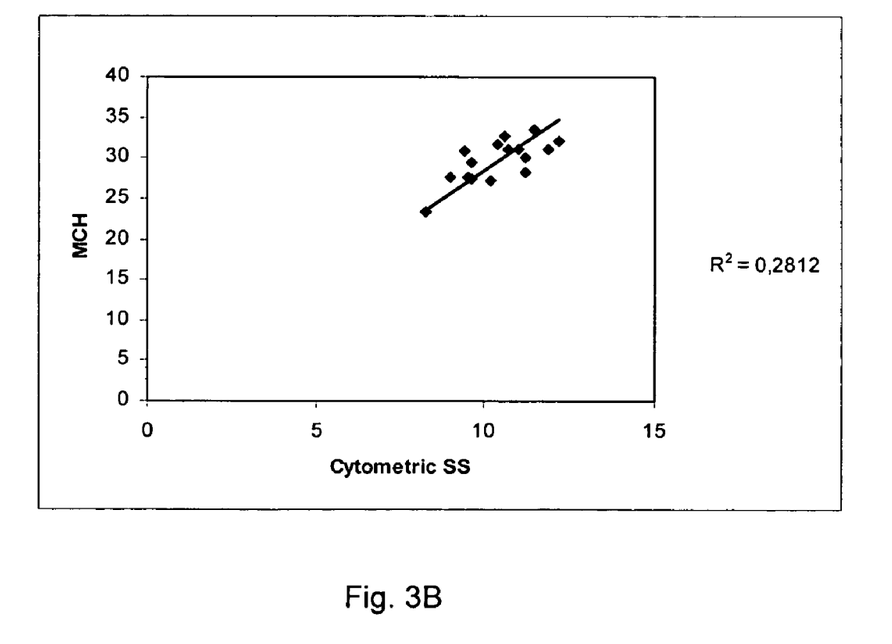
FIG. 3B shows the linear correlation curve of the mean side scatter values of the same blood samples obtained using a sphering reagent treatment and the MCH values.

The correlations of the obtained mean side scatter values from both aliquots of the samples to the MCH obtained on the hematology analyzer were analyzed separately. FIGS. 3A and 3B showed the result of the linear correlation analysis. As shown in FIG. 3A, the mean side scatter values obtaining using the method of the present invention had a good correlation with MCH, with a correlation coefficient ($r^2$) of 0.9202. This indicated that the side scatter signal obtained using the method of the present invention was a direct measurement of the cellular hemoglobin of a red blood cell. On the contrary, as shown in FIG. 3B the mean side scatter values obtaining using the sphering reagent treatment correlate poorly with MCH, with a correlation coefficient ($r^2$) of 0.2812.

As can be appreciated that upon obtaining cellular hemoglobin, the total hemoglobin concentration of the blood sample can be obtained by multiplying $Hgb_{cell}$ by the red blood cell count. The latter can be obtained either independently, or together with the measurement described above if the flow cytometric instrument has a fluid volume measuring device to facilitate the counting.

It should be understood that the cellular hemoglobin ($Hgb_{cell}$) described herein is the total hemoglobin content in an individual red blood cell, which includes all hemoglobin variants present in that cell. Furthermore, the mean side scatter value of a blood sample is the mean of the side scatter signals of all red blood cells measured, which includes both mature red blood cells and the immature red blood cells, such as reticulocytes, present in the blood sample.

In a further aspect, the present invention provides a method of measuring cellular hemoglobin of reticulocytes ($Hgb_{retic}$) in a blood sample. Herein, the term of cellular hemoglobin of reticulocytes ($Hgb_{retic}$) refers to the total hemoglobin in an individual reticulocyte, which includes all hemoglobin variants present in that cell. Cellular hemoglobin of reticulocytes is also commonly referred to as reticulocyte cellular hemoglobin (CHr), which is one of the reported parameters on Advia® 120 hematology analyzer manufactured by Bayer Diagnostics, Tarrytown, N.Y.

In order to measure cellular hemoglobin of the reticulocytes, it is necessary to differentiate the reticulocytes from the mature red blood cells that are the majority of the red blood cells. The method of the present invention, as fully described hereinafter, provides differentiation of reticulocytes and measurement of cellular hemoglobin of the reticulocytes in one signal step measurement on a flow cytometer.

In one embodiment, the method of measuring cellular hemoglobin of reticulocytes comprises the following steps:

(a) mixing an aliquot of a blood sample with a nucleic acid dye reagent to form a stained sample, and incubating the stained sample for a first period of time sufficient to permit binding of the dye to intracellular RNAs;

(b) mixing an aliquot of the stained sample with a permeation reagent to form a first sample mixture; and incubating the first sample mixture for a second period of time sufficient to allow the permeation reagent to permeate cellular membrane of the mature red blood cells and the reticulocytes and to cause hemoglobin aggregation within the cells;

(c) adding a neutralization reagent to the first sample mixture to form a second sample mixture; incubating the second sample mixture for a third period of time sufficient to inhibit further reactions of the permeation reagent with the red blood cells;

(d) performing a cell-by-cell measurement of side scatter signals and fluorescence signals at a predetermined wavelength, of the mature red blood cells and the reticulocytes in the second sample mixture on a flow cytometer;

(e) differentiating the reticulocytes from the mature red blood cells using the fluorescence measurement, or the combination of the fluorescence and the side scatter measurements; and (f) obtaining cellular hemoglobin ($Hgb_{retic}$) of the reticulocytes using the side scatter measurement.

Similar to the method of measuring cellular hemoglobin of a blood sample described above, the method of measuring cellular hemoglobin of reticulocytes preferably further includes addition of a fixation reagent to fix the cells prior to the measurement on the instrument.

The nucleic acid dye reagent is an aqueous solution, which comprises a fluorescent nucleic acid dye specific to RNA molecules, a surface active agent, and one or more salts to maintain the reagent isotonic. Preferably, acridin orange is used in the nucleic acid dye reagent as shown in Example 5. The surface active agent makes the cellular membrane permeable to small dye molecules. The sphering reagent shown in Example 4 contains n-dodecyl beta-D-maltoside. This surface active agent has been used for facilitating rapid staining of nucleic acids inside cells, as taught in U.S. Pat. No. 6,271,035, which is herein incorporated by reference in its entirety. The sphering reagent of Example 4 renders the cellular membrane sufficiently permeable to fluorescent dye molecules, however, it is not permeable to large biological molecules, such as antibodies. This reagent is used as a medium of the nucleic acid dye reagent. Preferably, the nucleic acid dye reagent is essentially neutral or slightly basic. It contains an organic buffer, for example a low concentration of HEPES. It has been found that phosphate should be avoided in the nucleic acid dye reagent, as it may interfere with the reaction of the permeation reagent. Moreover, optionally, the nucleic acid dye reagent further comprises a low concentration of a fixative and a saccharide, for example, formaldehyde and D (+) trehalose, for protecting the cells.

Preferably, a blood sample is diluted with the nucleic acid dye reagent about 50 times. The first period of time for incubation of the blood sample with the nucleic acid dye reagent is typically from about 30 seconds to about 3 minutes, preferably about one minute. After staining of the RNAs, an aliquot of the stained sample is mixed with the permeation reagent, preferably with a ratio of the permeation reagent to the stained sample of about 15:1 to about 100:1. After further addition of the neutralization reagent and the fixation reagent, the total dilution of the blood sample in the exemplary embodiment is about 4000 times. The incubation times for the first and the second sample mixtures, more specifically after addition of the permeation reagent and the neutralization reagent, respectively, have been described previously in the process of measuring cellular hemoglobin ($Hgb_{cell}$) of a blood sample.

It should be understood that for the purpose of staining RNAs in the reticulocytes, the nucleic acid dye can also be added into the permeation reagent or the neutralization reagent, instead of using a pre-staining step as described above. However, using the pre-staining step prior to the reaction with the permeation reagent and the neutralization reagent has practical advantages in the diagnostic analysis. Since only a small volume of the stained sample is used in the further treatment with the reagent system of the present invention, the dye concentration in the final sample mixture is very low, which improves the signal to background ratio of the fluorescence measurement and prevents non-specific binding of the dye to tubes, and other instrument components.

Figure 4A:
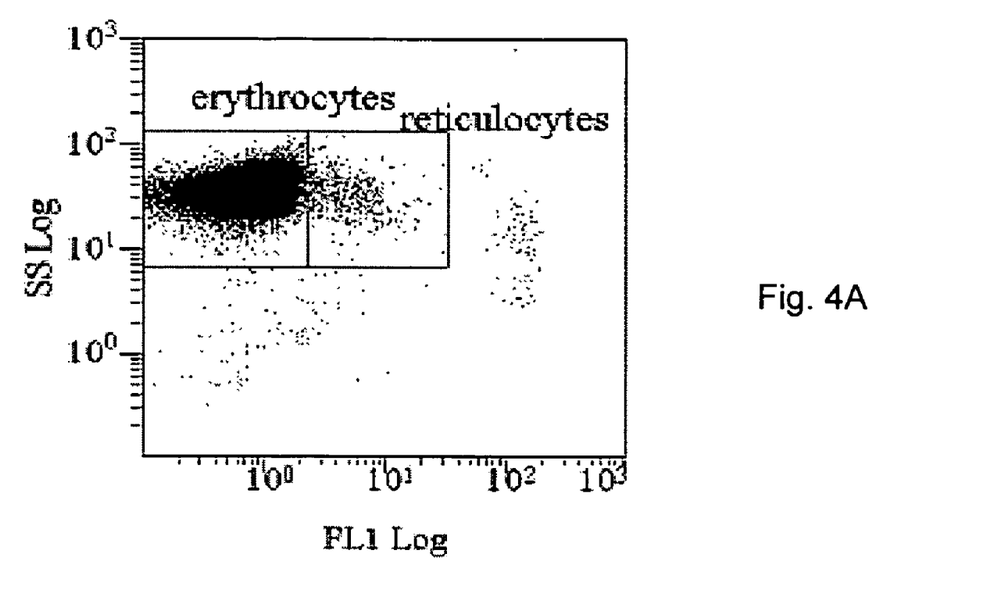
FIG. 4A shows the scattergram of side scatter vs. FL1 (in log scale) of a blood sample obtained using the method of one embodiment of the present invention.

Example 8 illustrates an example of simultaneous measurements of reticulocytes and cellular hemoglobin of the reticulocytes. The blood sample was mixed first with a nucleic acid dye reagent containing acridin orange to stain the nucleic acids, and then subsequently treated by the permeation reagent, the neutralization reagent and the fixation reagent. The prepared sample mixture was analyzed on a FC500 MPL flow cytometer. The obtained scattergram of side scatter vs. FL1 is shown in FIG. 4A. FL1 is the fluorescence signals measured at 488 nm, which are originated from stained RNAs in the reticulocytes.

Figure 4B:
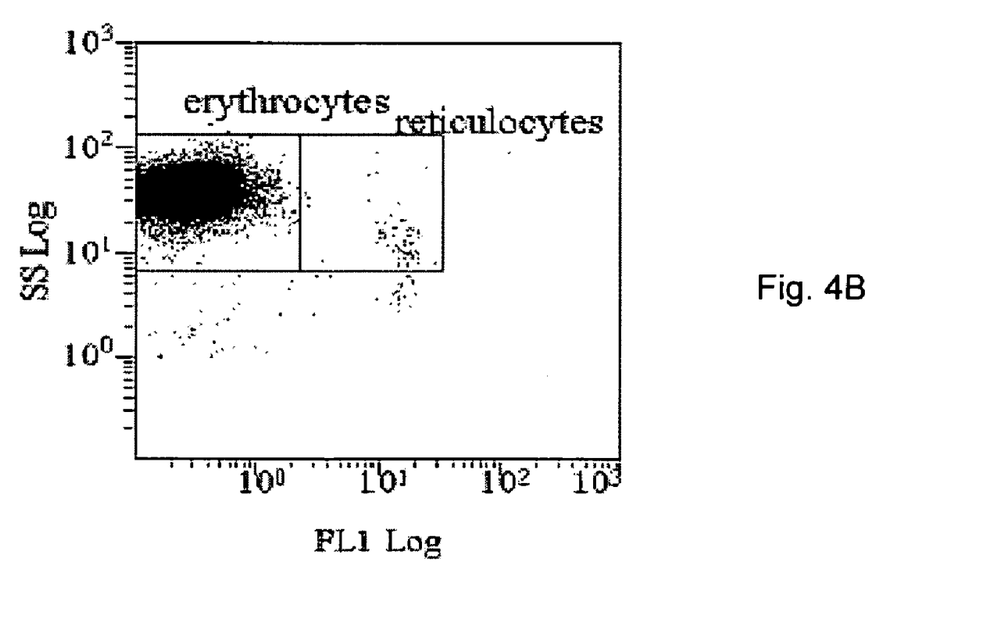
FIG. 4B is the scattergram of the same blood sample treated without using the nucleic acid dye reagent.

As shown in FIG. 4A, reticulocytes had substantially stronger fluorescence signals than the mature red blood cells. A cluster of reticulocytes located on the right side of the mature red blood cells in the scattergram. The reticulocytes can be differentiated from the mature red blood cells using either the histogram of FL1, or using the two dimensional scattergram of side scatter vs. FL1. As a comparison, the scattergram of an unstained blood sample is shown in FIG. 4B, wherein no separation of reticulocytes from the mature red blood cells could be appreciated.

A differential analysis of the scattergram shown in FIG. 4A was performed to separate reticulocytes from the mature red blood cells. The cellular hemoglobin of individual reticulocyte ($Hgb_{retic}$) was obtained from the side scatter signal of the individual reticulocyte, in the same manner described above for all red blood cells in the sample mixture.

In another aspect, the present invention provides a method of determining a cellular percentage of a hemoglobin variant of a blood sample. In one embodiment, the method comprises the following steps:

(a) mixing an aliquot of a blood sample with a permeation reagent to form a first sample mixture; and incubating the first sample mixture for a first period of time sufficient to permeate cellular membrane of red blood cells and to cause hemoglobin aggregation within the cells;

(b) adding a neutralization reagent that contains an antibody specific to a hemoglobin variant of interest to the first sample mixture to form a second sample mixture; incubating the second sample mixture for a second period of time sufficient to allow the antibody to bind to the hemoglobin variant within the cells, and inhibiting further reactions of the permeation reagent with the red blood cells;

(c) performing a cell-by-cell measurement of side scatter signals and fluorescence signals at a predetermined wavelength, of the red blood cells in the second sample mixture on a flow cytometer;

(d) obtaining cellular hemoglobin variant ($Hgb_{variant}$) and cellular hemoglobin ($Hgb_{cell}$) of the red blood cells using the obtained fluorescence and the side scatter signals; and (e) obtaining cellular percentage of the hemoglobin variant using the obtained $Hgb_{variant}$ and $Hgb_{cell}$.

Similarly, the fixation reagent can be added to the sample mixture prior to the measurement on the flow cytometer.

Herein, the term of hemoglobin variant includes all hemoglobin variants, for example fetal hemoglobin, glycated hemoglobin ($Hb_{A1c}$), and aberrant forms of hemoglobin, such as those found in sickle cell disease and thalassemia. The term of cellular hemoglobin variant ($Hgb_{variant}$) is the amount of a hemoglobin variant in an individual red blood cell. The term of cellular percentage of a hemoglobin variant refers to the percentage of a specific hemoglobin variant of the total hemoglobin in an individual red blood cell. Using the terms defined above, cellular percentage of a hemoglobin variant is the ratio of $Hgb_{variant}$ and $Hgb_{cell}$ multiplying by the factor of 100.

As described above, an antibody specific to a hemoglobin variant of interest can be added into the neutralization reagent. Upon reaction with the permeation reagent, the cellular membrane becomes permeable to these large antibody molecules. The antibodies penetrate the cellular membrane and bind to the antigen sites of the intracellular proteins. In the method of measuring $Hb_{A1c}$, a fluorescent monoclonal anti-$Hb_{A1c}$ antibody is used. Herein, the term of fluorescent antibody refers to an antibody which is covalently conjugated to a fluorescent dye.

In one embodiment, the fluorescent monoclonal anti-$Hb_{A1c}$ antibody is anti-$Hb_{A1c}$-FITC antibody, which has fluorescein N-isothiocyanate (FITC) covalently conjugated to anti-$Hb_{A1c}$ antibody. FITC has the absorption maximum at 525 nm. In another embodiment, the fluorescent anti-$Hb_{A1c}$ antibody is anti-$Hb_{A1c}$-Alexa Fluor 647 antibody, which was prepared by covalently binding a fluorescent dye Alexa Fluor 647 to the antibody. Alexa Fluor 647 has the absorption maximum at 647 nm.

The incubation times for the first and the second sample mixtures, more specifically after addition of the permeation reagent and the neutralization reagent, respectively, have been described previously in the process of measuring cellular hemoglobin ($Hgb_{cell}$) of a blood sample.

Example 9 illustrates an example of measuring $Hb_{A1c}$ in the reticulocytes and the mature red blood cells using anti-$Hb_{A1c}$-Alexa Fluor 647 antibody. However, it can be appreciated that the same method can also be used for measuring $Hb_{A1c}$ of all red blood cells, without the step of staining the RNAs. In the measurement of $Hb_{A1c}$ of all red blood cells no differentiation of reticulocytes from the matured red blood cells is needed.

On a flow cytometer, a reference control is commonly used to calibrate the instrument. The reference control is typically made of fluorescent particles with known hemoglobin concentration, or equivalent hemoglobin concentration, known side scatter and fluorescence intensities. These typically include, but are not limited to, synthetic particles, human or animal blood cells, and processed human or animal blood cells. Upon calibration, quantitative measurement of cellular $Hb_{A1c}$, i.e., the absolute amount of this hemoglobin variant in the individual red blood cell can be achieved on the flow cytometer.

In yet a further aspect, the present invention provides a method of measuring cellular hemoglobin variant of the reticulocytes in a blood sample. The term of cellular hemoglobin variant of reticulocytes ($Hgb_{variant-retic}$) is the amount of a hemoglobin variant in an individual reticulocyte.

In one embodiment, the method measuring cellular hemoglobin variant of the reticulocytes comprises the following steps:

(a) mixing an aliquot of the blood sample with a nucleic acid dye reagent to form a stained sample, and incubating the stained sample for a period of time sufficient to permit the dye to bind to intracellular RNAs;

(b) mixing an aliquot of the stained sample with a permeation reagent to form a first sample mixture; and incubating the first sample mixture for a period of time sufficient to allow the permeation reagent to permeate cellular membrane of mature red blood cells and reticulocytes, and to cause hemoglobin aggregation within the cells;

(c) adding a neutralization reagent containing a fluorescent antibody specific to the hemoglobin variant of interest to the first sample mixture to form a second sample mixture; incubating the second sample mixture for a period of time sufficient to permit binding of the antibody to the hemoglobin variant within the cells, and inhibiting further reactions of the permeation reagent with the mature red blood cells and the reticulocytes;

(d) performing a cell-by-cell measurement of fluorescence signals at two predetermined wavelengths of the mature red blood cells and the reticulocytes in the second sample mixture by on a flow cytometer; and (e) differentiating the reticulocytes from the mature red blood cells, and obtaining cellular hemoglobin variant in each reticulocyte ($Hgb_{variant-retic}$) using the fluorescence signals.

The incubation times after addition of each reagent have been described above.

As can be understood from the above descriptions, the method can further include performing a cell-by-cell measurement of side scatter signals of the red blood cells in the second sample mixture in step (d). Upon differentiation of reticulocytes, cellular hemoglobin of each reticulocyte ($Hgb_{retic}$) can be obtained using the side scatter signals. Then, using $Hgb_{variant-retic}$ and $Hgb_{retic}$, the cellular percentage of the hemoglobin variant in each reticulocyte can be obtained.

Figure 5A:
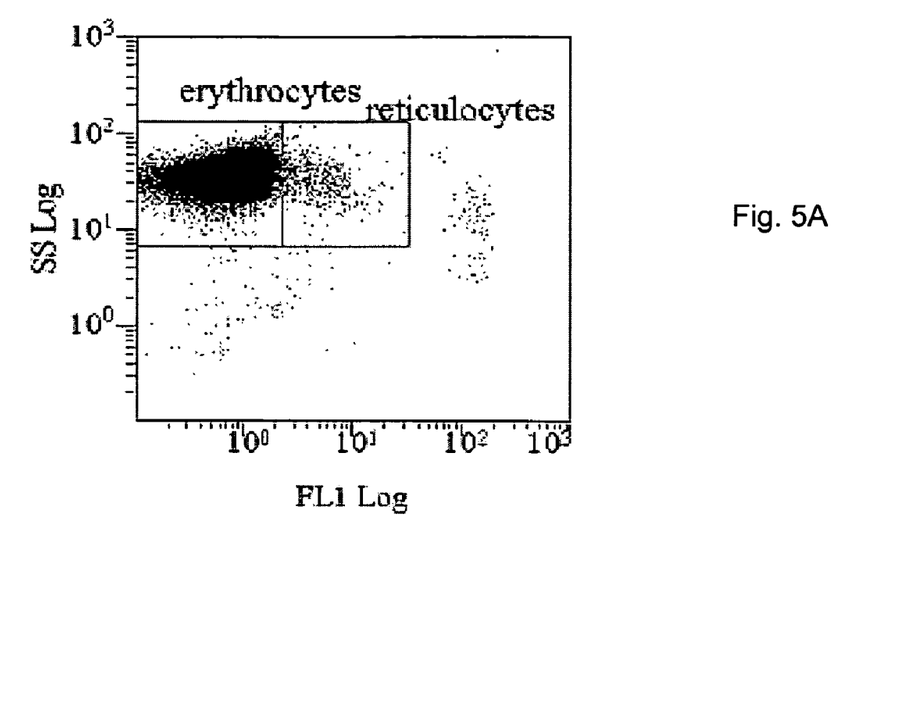
FIGS. 5A and 5B show the scattergrams of side scatter vs. FL1 (in log scale) and FL1 vs. FL4 (in semi-log scale) of a blood sample, respectively, obtained in a simultaneous measurement of side scatter and fluorescence at two wavelengths for determination of $Hb_{A1c}$ of reticulocytes and of mature red cells separately.

Example 9 illustrates an example of measuring $Hb_{A1c}$ and cellular hemoglobin of the reticulocytes and the mature red blood cells in a blood sample. A blood sample was mixed first with a nucleic acid dye reagent containing acridin orange to stain the nucleic acids, and subsequently treated with the permeation reagent. Then a neutralization reagent containing anti-$Hb_{A1c}$-Alexa Fluor 647 antibody was added, and the sample mixture was incubated to permit binding of the antibody to $Hb_{A1c}$. A fixation reagent was further added to fix the blood cells. The prepared sample mixture was aspirated into a FC500 MPL flow cytometer, and a cell-by-cell measurement of side scatter signals and fluorescence signals at 488 nm (FL1) and 647 nm (FL4) was made on the instrument. The obtained scattergrams of side scatter vs. FL1, and FL1 vs. FL4 are shown in FIGS. 5A and 5B, respectively.

The reticulocytes were differentiated from the mature red blood cells by a differential analysis using the side scatter vs. FL1 scattergram. Cellular hemoglobin of the reticulocytes ($Hgb_{retic}$) and the mature red blood cells ($Hgb_{cell}$) was obtained using the side scatter signals, as described above.

Figure 5B:
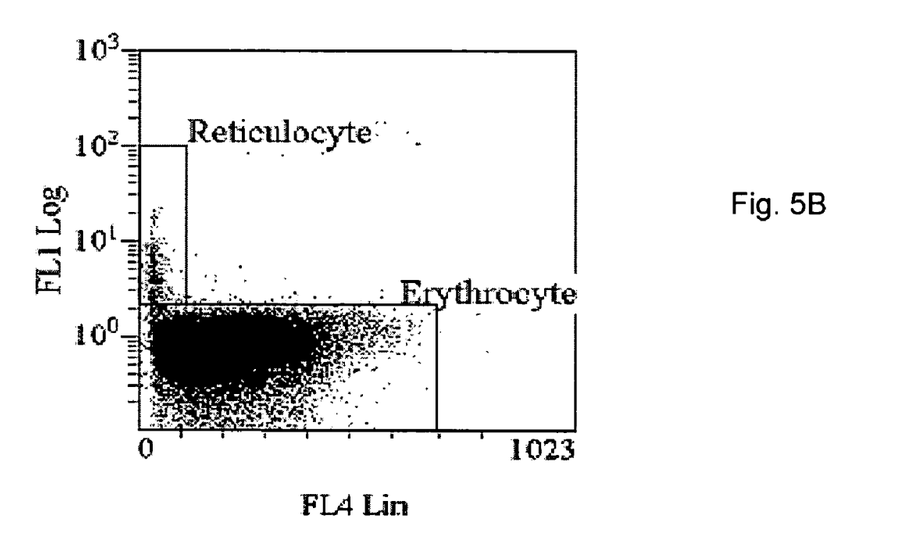

As shown in FIG. 5B, reticulocytes were also separated from the mature red blood cells in this scattergram. $Hb_{A1c}$ of an individual reticulocyte or an individual mature red blood cell was measured using the FL4 signal of that cell. Using a reference control, such as fluorescent beads or cells labeled with the same dye, cellular glycated hemoglobin of the reticulocyte ($Hb_{A1c-retic}$) and the mature red blood cell ($Hb_{A1c}$) was obtained. From the ratio of $Hb_{A1c-retic}$ and $Hgb_{retic}$, a percentage of $Hb_{A1c}$ in the individual reticulocyte was obtained. Similarly, from the ratio of $Hb_{A1c}$ and cellular hemoglobin of the mature red blood cells, a percentage of $Hb_{A1c}$ in the individual mature red blood cell was obtained.

The following examples are illustrative of the invention and are in no way to be interpreted as limiting the scope of the invention, as defined in the claims. It will be understood that various other ingredients and proportions may be employed, in accordance with the proceeding disclosure.

EXAMPLE 1

Permeation Reagent Compositions

Composition A

Following permeation reagent composition was prepared:

| Component | Concentration |
|---|---|
| N-lauroyl sarcosine | 2.3 mM |
| Pyrrolidine and HCl | quantity to adjust pH to 5.3 |

More specifically, a stock solution of N-lauroyl sarcosine made first. 1.0 g of N-lauroyl sarcosine (Fluka) was pre-dissolved in 1.5 ml of ethanol (96%). 180 µl of pyrrolidine (Aldrich) was added into 95 ml of deionized water. Then the N-lauroyl sarcosine/ethanol solution was added into the pyrrolidine solution; the pH was adjusted to 5.6 by pyrrolidine and HCl, and the volume was adjusted to 100 ml with deionized water to form the stock solution. The total volume of the reagent is adjusted to 100 ml with deionized water. The permeation reagent composition was prepared by diluting 6.25 ml of the stock solution with deionized water to 100 ml and adjusting pH to 5.3 with pyrrolidine and HCl. The reagent was filtered through a sterile nylon filter of 0.22 µm pore size. The Composition A had a conductivity of 0.1 mS/cm.

Composition B

Following permeation reagent composition was prepared:

| Component | Concentration |
|---|---|
| N-lauroyl sarcosine | 2.3 mM |
| Bovine serum albumin | 1.1 g/l |
| Glycerol | 1.08 M |
| Pyrrolidine and HCl | quantity to adjust pH to 5.3 |

The reagent composition had a conductivity of 0.25 mS/cm. N-lauroyl sarcosine was added as the stock solution, as described above.

Composition C

Following permeation reagent composition was prepared:

| Component | Concentration |
|---|---|
| N-lauroyl sarcosine | 2.2 mM |
| Tris lauryl sulphate | 0.5 mM |
| Succinic acid | 4 mM |
| Boric acid | 40 mM |
| D (+) glucose | 166 mM |
| Pyrrolidine and HCl | quantity to adjust pH to 5.0 |

The reagent composition had a conductivity of 0.5 mS/cm. N-lauroyl sarcosine was added as the stock solution, as described above.

Composition D

Following permeation reagent was prepared according to the following composition:

| Component | Concentration |
|---|---|
| N-lauroyl sarcosine | 2.03 mM |
| Succinic acid | 10 mM |
| Sucrose | 0.22 M |
| Bovine serum albumin | 0.015 mM |
| Proclin 300 | 0.5 ml/l |
| Pyrrolidine | quantity to adjust pH at 5.4 |

More specifically, sucrose, proclin-300, succinic acid and 1.2 ml of pyrrolidine were mixed with 900 ml of deionized water first. The N-lauroyl sarcosine was added and the mixture was agitated until N-lauroyl sarcosine was completely dissolved. Then, bovine serum albumin was added and dissolved. The volume was adjusted to about 99% of the final volume of 1 liter and the pH was adjusted with diluted pyrrolidine (10% v/v) to 5.4. The pH adjustment could be made with 1M hydrochloric acid. The reagent volume was adjusted to 1 liter and the reagent was filtered through a sterile nylon filter of 0.22 µm pore size. The reagent had a conductivity of 0.99 mS/cm and osmolality of 268 mOsm/Kg $H_2O$. Proclin 300 was obtained from Zymed laboratories, South San Francisco, Calif.

EXAMPLE 2

Neutralization Reagent Composition

An aqueous neutralization reagent was prepared according to the following composition:

| Component | Concentration |
|---|---|
| HEPES | 40 mM |
| Sodium chloride | 0.5 M |
| Bovine serum albumin | 0.91 mM |
| Sodium azide | 0.03 M |
| Sodium hydroxide | quantity to adjust pH at 7.25 |

More specifically, HEPES, sodium chloride, and bovine serum albumin were dissolved in deionized water first. The reagent volume was adjusted to about 60% of the final volume. 1 M sodium hydroxide was added to adjust the pH to 7.0. Sodium azide was added, the volume was adjusted to about 95% of the final volume and the pH was further adjusted with 1 M sodium hydroxide to 7.25. The reagent volume was adjusted to the final volume and the reagent was filtered through a sterile nylon filter of 0.22 µm pore size. The reagent had an osmolality of 1,095 mOsm/Kg $H_2O$.

EXAMPLE 3

Fixation Reagent Composition

An aqueous fixation reagent was prepared according to the following composition:

| Component | Concentration |
|---|---|
| Sodium chloride | 155 mM |
| Disodium hydrogen phosphate dihydrate | 40 mM |
| Formaldehyde | 0.62 M |
| Boric acid | 180 mM |

-continued

| Component | Concentration |
|---|---|
| EGTA | 10 mM |
| Dextrane sulfate (MW 500.000) | 0.016 µM |

More specifically, the components were dissolved in deionized water at about 90% of the final volume. The pH was adjusted to 7.1 using 1 M sodium hydroxide or 1 M hydrochloric acid. The reagent volume was adjusted to the final volume and the reagent was filtered through a sterile nylon filter of 0.22 µm pore size. The reagent had an osmolality of 1,348 mOsm/Kg $H_2O$.

EXAMPLE 4

Sphering Reagent Composition

An aqueous sphering reagent was prepared according to the following composition:

| Component | Concentration |
|---|---|
| Sodium chloride | 0.137 M |
| HEPES | 0.005 M |
| D(+) Trehalose | 0.0005 M |
| Formaldehyde | 0.083 M |
| n-Dodecyl beta-D-maltoside | 0.04 mM |
| Proclin-300 | 0.5 ml/l |
| Sodium hydroxide | quantity to adjust pH at 7.5 |

More specifically, the components, except sodium hydroxide, were mixed in deionized water. The reagent volume was adjusted to about 90% of the final volume. The pH was adjusted using 1M sodium hydroxide. The reagent volume was adjusted to the final volume and the reagent was filtered through a sterile nylon filter of 0.22 µm pore size.

EXAMPLE 5

Nucleic Acid Dye Reagent Composition

Acridin orange was added into the sphering reagent of Example 4 to form a nucleic acid dye reagent which had an acridin orange concentration of 0.5 mg/l. The nucleic acid dye reagent was filtered again through a sterile nylon filter of 0.22 µm pore size.

EXAMPLE 6

Effect of the Permeation Reagent on Different Components of the Red Blood Cells

A quantity of blood, treated with 0.7 mM of ethylenediamine tetraacetic acid (EDTA) as anticoagulant, was used to prepare blood serum. Another quantity of the EDTA treated blood was washed with phosphate buffered saline (PBS), and diluted with nine volumes of water to obtain a cell lysate. The cell lysate was subjected to centrifugation at 2000 g for 15 minutes to separate the soluble cell fraction and the membrane fraction. The pellet containing the membrane fraction was mixed with a volume of water, which contains 5% in volume of the soluble cell fraction.

Precipitation of the serum, soluble cell fraction, membrane fraction, as well as bovine serum albumin as a control, was monitored after mixing with the Composition C of Example 1, and with the following modified reagents:

1. Modified Reagent 1: Composition C of Example 1 without addition of the surfactants (Tris lauryl sulphate and N-lauroyl sarcosine), having a pH of 7.0.
2. Modified Reagent 2: Composition C of Example 1 without addition of the surfactants (Tris lauryl sulphate and N-lauroyl sarcosine), having a pH of 5.0.
3. Modified Reagent 3: Composition C of Example 1, having a pH of 7.0.
4. Permeation Reagent 4: Composition C of Example 1 as described (pH 5.0).

Sample mixtures were produced by mixing 2 ml of a specific reagent described above with one of the following four components:
- 0.01 ml of serum (A),
- 0.01 ml of a preparation of bovine albumin at 15% weight/volume (B),
- 0.1 ml of soluble cell fraction (C), and
- 0.1 ml of membrane fraction (D).

To determine the precipitation of the proteins one hour after preparation of the sample mixtures, the optical density of the sample mixtures was measured at 650 nm, the wavelength at which hemoglobin, the principal constituent of the fractions, does not absorb.

FIG. 1 shows the effect of the reagents on the precipitation of the cellular components in: serum; a preparation of bovine serum albumin (BSA) at 15% weight/volume; soluble cell fraction (cytosol); and membrane fraction. The bar graph for each of the above referenced cellular components shows the results, from the left to right, obtained using the Modified Reagents 1 to 3 and the Permeation Reagent 4.

FIG. 1 shows that only the Permeation Reagent 4, which contained the surfactants with a pH between 4 and 6 as described above, caused aggregation and precipitation of proteins, with the exception of bovine serum albumin (BSA).

EXAMPLE 7

Measurement of Cellular Hemoglobin of a Blood Sample

4 µl of a blood sample was mixed with 200 µl of the sphering reagent of Example 4. After 1 minute of incubation, 3 µl of the suspension was subsequently mixed with 60 µl of the permeation reagent Composition D of Example 1. After 2.5 minutes of incubation, 100 µl of the neutralization reagent of Example 2 was added. After another 10 minute incubation, 80 µl of the fixation reagent of Example 3 was added.

16 whole blood samples were collected from 16 different patients. An aliquot of each sample was prepared using the above described procedure. The formed sample mixtures were analyzed on a FC500 MPL cytometer. FIG. 2A showed the obtained scattergram of forward scatter vs. side scatter of one of the blood samples. The major population of cells shown was the treated red blood cells, and the mean side scatter value of the cells in this population was measured for each blood sample analyzed. It is noted that the minor population in the scattergram was doublets originated from aggregated cells. This population was about 1% of the total red blood cells measured, and they were not considered in the determination of the mean side scatter value.

For the purpose of comparison, another aliquot from each of these 16 samples was prepared using the sphering reagent, without the reagent system of the present invention. 4 µl of a blood sample was mixed with 200 µl of the sphering reagent of Example 4. After 1 minute of incubation, 3 µl of the suspension was mixed with 240 μl of phosphate buffered saline (PBS) to form a sphered sample. The sphered sample was analyzed on the same FC500 MPL cytometer. FIG. 2B showed the scattergram of forward scatter vs. side scatter of the same blood sample shown in FIG. 2A.

As shown, the mean side scatter value of the blood sample obtained using the method of the present invention was substantially higher than the mean side scatter value of the blood sample obtained using the treatment of the sphering reagent and PBS. Among these 16 blood samples, the mean side scatter values obtained using the method of the present invention were in average about 4 to 5 times higher.

These 16 whole blood samples were also analyzed on a Sysmex XE 2100 hematological analyzer (Sysmex Corporation, Kobe, Japan), equipped with the reagents provided by manufacturer and operated on the standard condition. Mean corpuscular hemoglobin (MCH) was obtained for each of the blood samples from the red cell index reported by the analyzer. MCH (pg) was calculated from the total hemoglobin concentration (Hgb, g/dl) of a lysed blood sample and the red blood cell count (RBC, $10^{12}$/l) of the blood sample. It is noted that MCH can also be expressed in attomol, which is calculated by dividing picogram by the molecular weight of hemoglobin.

The correlations of the obtained mean side scatter values from both aliquots of the samples to the MCH values obtained on the hematology analyzer were analyzed separately. FIGS. 3A and 3B showed the result of the linear correlation analysis. As shown in FIG. 3A, the mean side scatter values (labeled as Cytometric SS) obtaining using the method of the present invention had a good correlation with MCH, with a correlation coefficient ($r^2$) of 0.9202. This indicated that the side scatter signal obtained using the method of the present invention was a direct measurement of the cellular hemoglobin of a red blood cell. On the contrary, as shown in FIG. 3B the mean side scatter values obtaining using the sphering reagent treatment correlate poorly with MCH, with a correlation coefficient ($r^2$) of 0.2812.

EXAMPLE 8

Measurement of Cellular Hemoglobin of Reticulocytes in a Blood Sample

4 μl of a whole blood sample was mixed with 200 μl of the nucleic acid dye reagent of Example 5. After 1 minute of incubation, 3 μl of the suspension was subsequently mixed with 60 μl of the permeation reagent Composition D of Example 1. After 2.5 minutes of incubation, 100 μl of the neutralization reagent of Example 2 was added. After another 10 minute incubation, 80 μl of the fixation reagent of Example 3 was added.

The sample mixture obtained was analyzed on a FC500 MPL cytometer by side scatter measurement and fluorescence measurement at 488 nm (FL1). FIG. 4A showed the obtained scattergram of side scatter vs. FL1.

Another aliquot of the same sample was treated using the same procedure except that instead of the nucleic acid dye reagent, the sphering reagent of Example 4 was used. The sample mixture was analyzed on the same FC500 MPL cytometer by side scatter and fluorescence measurements. FIG. 4B showed the scattergram of side scatter vs. FL1.

As shown in FIG. 4A, reticulocytes had stronger fluorescence signals and a cluster of reticulocytes located on the right side of the mature red blood cells. The reticulocytes could be differentiated from the mature red blood cells either using the histogram of FL1, or using the two dimensional scattergram. On the contrary, in FIG. 4B no reticulocyte was separated from the mature red blood cells, when an unstained sample was used.

It is noted that the scattergram shown did not gate out the white blood cells, which showed in right side of the scattergram of FIG. 4A and showed in the lower right quadrant of the marked reticulocyte region in FIG. 4B.

A differential analysis using the scattergram as shown in FIG. 4A was performed to separate reticulocytes from the mature red blood cells. The cellular hemoglobin of individual reticulocytes ($Hgb_{retic}$) was obtained from the side scatter signals of the individual reticulocytes, in the same manner described previously in Example 7.

EXAMPLE 9

Measurement of $Hb_{A1c}$ and Cellular Hemoglobin of Reticulocytes and Mature Red Blood Cells in a Blood Sample 4 μl of a blood sample was mixed with 200 μl of a nucleic acid dye reagent of Example 5. After 1 minute of incubation, 3 μl of the suspension was mixed with 60 μl of the permeation reagent Composition D of Example 1. After 2.5 minutes of incubation, 100 μl of a neutralization reagent containing a fluorescent anti-$Hb_{A1c}$ antibody was added. The neutralization reagent comprised the neutralization reagent of Example 2 and 5 mg/l of monoclonal anti-$Hb_{A1c}$ antibody covalently conjugated to fluorescence dye Alexa Fluor 647. After another 10 minute incubation, 80 μl of the fixation reagent of Example 3 was added to form a final sample mixture.

The final sample mixture was analyzed on a FC500 MPL cytometer by side scatter measurement and fluorescence measurements at 488 nm (FL1) and 647 nm (FL4). FIG. 5A showed the obtained scattergram of side scatter vs. FL1. The reticulocytes were differentiated from the mature red blood cells by a differential analysis of this scattergram. The cellular hemoglobin of individual reticulocytes ($Hgb_{retic}$) and individual mature red blood cells ($Hgb_{cell}$) was obtained using the side scatter signals, as described above in Examples 7 and 8.

FIG. 5B showed the scattergram of FL1 vs. FL4 obtained from the measurements. As shown, reticulocytes were also separated from the mature red blood cells in this scattergram. $Hb_{A1c}$ of an individual reticulocyte or an individual mature red blood cell was measured using the FL4 signal of that cell. Using a reference control, such as fluorescent beads or cells labeled with the same dye, cellular glycated hemoglobin of the reticulocyte ($Hb_{A1c\text{-}retic}$) and the mature red blood cell was obtained. From the ratio of $Hb_{A1c\text{-}retic}$ and $Hgb_{retic}$, a percentage of $Hb_{A1c}$ in the individual reticulocyte was obtained. Similarly, from the ratio of $Hb_{A1c}$ and cellular hemoglobin of the mature red blood cells, a percentage of $Hb_{A1c}$ in the individual mature red blood cell was obtained.

The anti-$Hb_{A1c}$ antibody was produced in a mouse hyper immunized against normal human hemoglobin. The normal human hemoglobin contained approximately 5% of glycated hemoglobin $Hb_{A1c}$. The specificity of the antibody was shown by a positive reaction in a bead assay with a glycosilated tri-peptide of the three N-terminal residues of the human beta-hemoglobin chain, i.e., valine, leucine and histidine, respectively. The antibody did not react with the unglycosylated tri-peptide.

The fluorescent anti-$Hb_{A1c}$ antibody was prepared by covalently binding a fluorescent dye molecule, Alexa Fluor 647, to the monoclonal anti-$Hb_{A1c}$ antibody at a molecular ratio of five dye molecules per antibody molecules, according to the manufacturer's instructions. Alexa Fluor 647 is manufactured by Invitrogen Corporation, Carlsbad, Calif. The dye has the absorption maximum at 647 nm.

While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents.

What is claimed is:

1. A method of measurement of cellular hemoglobin of a blood sample comprising the steps of:
    (a) mixing an aliquot of a whole blood sample with a permeation reagent to form a first sample mixture; and incubating said first sample mixture for a first period of time sufficient to permeate the cellular membrane of red blood cells and cause hemoglobin aggregation within said red blood cells; wherein said permeation reagent comprises a N-acyl sarcosine or a salt thereof represented by the following molecular structure: $R_1$—CO—$N(CH_3)CH_2COOX_1$, wherein $R_1$ is an alkyl or alkylene group having 8 to 18 carbon atoms, and $X_1$ is H, $Na^+$, or $K^+$; and said permeation reagent has a pH between 4 and 6 and a low ionic strength defined by conductivity of less than 9 mS/cm;
    (b) adding a neutralization reagent to said first sample mixture to form a second sample mixture, and incubating said second sample mixture for a second period of time sufficient to inhibit further reactions of said permeation reagent with said red blood cells;
    (c) performing a cell-by-cell measurement of side scatter signals of said red blood cells in said second sample mixture on a flow cytometer; and
    (d) obtaining cellular hemoglobin ($Hgb_{cell}$) of said red blood cells of said blood sample using side scatter signals.

2. The method of claim 1 further comprising adding a fixation reagent into said second sample mixture to fix said red blood cells, prior to said performing measurement on said flow cytometer.

3. A method of measurement of cellular hemoglobin of reticulocytes in a blood sample comprising the steps of:
    (a) mixing an aliquot of a whole blood sample with a nucleic acid dye reagent to form a stained sample, and incubating said stained sample for a first period of time sufficient to allow said dye to bind to intracellular RNA;
    (b) mixing an aliquot of said stained sample with a permeation reagent to form a first sample mixture; and incubating said first sample mixture for a second period of time sufficient to allow said permeation reagent to permeate the cellular membrane of mature red blood cells and reticulocytes and cause hemoglobin aggregation within said mature red blood cells and said reticulocytes; wherein said permeation reagent comprises a N-acyl sarcosine or a salt thereof represented by the following molecular structure: $R_1$—CO—$N(CH_3)CH_2COOX_1$, wherein $R_1$ is an alkyl or alkylene group having 8 to 18 carbon atoms, and $X_1$ is H, $Na^+$, or $K^+$; and said permeation reagent has a pH between 4 and 6 and a low ionic strength defined by conductivity of less than 9 mS/cm;
    (c) adding a neutralization reagent to said first sample mixture to form a second sample mixture; incubating said second sample mixture for a third period of time sufficient to inhibit further reactions of said permeation reagent with said mature red blood cells and said reticulocytes;
    (d) performing a cell-by-cell measurement of side scatter signals and fluorescence signals, at a predetermined wavelength, of said mature red blood cells and said reticulocytes in said second sample mixture on a flow cytometer;
    (e) differentiating said reticulocytes from said mature red blood cells using said fluorescence signals, or a combination of said fluorescence signals and said side scatter signals; and
    (f) obtaining cellular hemoglobin ($Hgb_{retic}$) of said reticulocytes using said side scatter measurement.

4. The method of claim 3 further comprising adding a fixation reagent into said second sample mixture to fix said reticulocytes, prior to said performing measurement on said flow cytometer.

5. The method of claim 3, wherein said nucleic acid dye reagent comprises acridine orange.

6. A method of determining a cellular percentage of a hemoglobin variant of a blood sample comprising the steps of:
    (a) mixing an aliquot of a whole blood sample with a permeation reagent to form a first sample mixture; and incubating said first sample mixture for a first period of time sufficient to allow said permeation reagent to permeate the cellular membrane of red blood cells and cause hemoglobin aggregation within said red blood cells; wherein said permeation reagent comprises a N-acyl sarcosine or a salt thereof represented by the following molecular structure: $R_1$—CO—$N(CH_3)CH_2COOX_1$, wherein $R_1$ is an alkyl or alkylene group having 8 to 18 carbon atoms, and $X_1$ is H, $Na^+$, or $K^+$; and said permeation reagent has a pH between 4 and 6 and a low ionic strength defined by conductivity of less than 9 mS/cm;
    (b) adding a neutralization reagent containing a fluorescent antibody specific to said hemoglobin variant to said first sample mixture to form a second sample mixture; incubating said second sample mixture for a second period of time sufficient to permit said antibody to bind to said hemoglobin variant within said cellular membrane, and inhibiting further reactions of said permeation reagent with said red blood cells;
    (c) performing a cell-by-cell measurement of side scatter signals and fluorescence signals, at a predetermined wavelength, of said red blood cells in said second sample mixture on a flow cytometer;
    (d) obtaining cellular hemoglobin variant ($Hgb_{variant}$) and cellular hemoglobin ($Hgb_{cell}$) of said red blood cells using fluorescence signals and said side scatter signals obtained in step (c); and
    (e) obtaining cellular percentage of said hemoglobin variant using said $Hgb_{variant}$ and $Hgb_{cell}$, obtained in step (d).

7. The method of claim 6 further comprising adding a fixation reagent into said second sample mixture to fix said red blood cells, prior to said performing measurement on said flow cytometer.

8. The method of claim 6, wherein said hemoglobin variant is a glycated hemoglobin, fetal hemoglobin, or an aberrant form of hemoglobin.

9. The method of claim 6, wherein said hemoglobin variant is glycated hemoglobin ($Hb_{A1c}$).

10. The method of claim 9, wherein said fluorescent antibody is an anti-$Hb_{A1c}$ antibody.

11. The method of claim 10, wherein said anti-$Hb_{A1c}$ antibody is a monoclonal anti-$Hb_{A1c}$-sulfonated carbocyanine (Alexa Fluor 647) antibody.

12. A method of measurement of cellular hemoglobin variant of reticulocytes in a blood sample comprising the steps of:
   (a) mixing an aliquot of a whole blood sample with a nucleic acid dye reagent to form a stained sample, and incubating said stained sample for a first period of time sufficient to permit said dye to bind to intracellular RNAs;
   (b) mixing an aliquot of said stained sample with a permeation reagent to form a first sample mixture; and incubating said first sample mixture for a second period of time sufficient to allow said permeation reagent to permeate the cellular membrane of mature red blood cells and reticulocytes and cause hemoglobin aggregation within said mature red blood cells and said reticulocytes; wherein said permeation reagent comprises a N-acyl sarcosine or a salt thereof represented by the following molecular structure: $R_1$—CO—$N(CH_3)CH_2COOX_1$, wherein $R_1$ is an alkyl or alkylene group having 8 to 18 carbon atoms, and $X_1$ is H, $Na^+$, or $K^+$; and said permeation reagent has a pH between 4 and 6 and a low ionic strength defined by conductivity of less than 9 mS/cm;
   (c) adding a neutralization reagent containing a fluorescent antibody specific to a hemoglobin variant to said first sample mixture to form a second sample mixture; incubating said second sample mixture for a third period of time sufficient to permit binding of said antibody to said hemoglobin variant within said cellular membrane, and inhibiting further reactions of said permeation reagent with said mature red blood cells and said reticulocytes;
   (d) performing a cell-by-cell measurement of side scatter signals and fluorescence signals at two predetermined wavelengths of said mature red blood cells and said reticulocytes in said second sample mixture on a flow cytometer; and
   (e) differentiating said reticulocytes from said mature red blood cells, and obtaining cellular hemoglobin variant of said reticulocytes ($Hgb_{variant-retic}$) using said fluorescence signals obtained in step (d); and obtaining cellular hemoglobin of said reticulocytes ($Hgb_{retic}$) using said side scatter signals obtained in step (d).

13. The method of claim 12 further comprising adding a fixation reagent into said second sample mixture to fix said reticulocytes, prior to said performing measurement on said flow cytometer.

14. The method of claim 12, wherein said nucleic acid dye reagent comprises acridine orange.

15. The method of claim 12, wherein said hemoglobin variant is a glycated hemoglobin, fetal hemoglobin, or an aberrant form of hemoglobin.

16. The method of claim 12, wherein said hemoglobin variant is glycated hemoglobin ($Hb_{A1c}$).

17. The method of claim 12, wherein said fluorescent antibody is a monoclonal anti-$Hb_{A1c}$ antibody.

18. The method of claim 12, wherein the method further comprises obtaining cellular percentage of said hemoglobin variant of said reticulocytes using said $Hgb_{variant-retic}$ and said $Hgb_{retic}$.

19. The method of claim 18, wherein said cell-by-cell measurement further comprises obtaining said cellular hemoglobin variant of said mature red blood cells using said fluorescence signals at one of said predetermined wavelengths obtained in step (d).

20. The method of claim 19, wherein said cell-by-cell measurement further comprises obtaining cellular hemoglobin of said mature red blood cells using said side scatter signals; and obtaining cellular percentage of said hemoglobin variant of said mature red blood cells using said cellular hemoglobin variant and said cellular hemoglobin of said mature red blood cells.

* * * * *